United States Patent [19]
Houpis et al.

[11] Patent Number: 5,728,838
[45] Date of Patent: Mar. 17, 1998

[54] METHOD OF PREPARING PHOSPHODIESTERASE IV INHIBITORS

[75] Inventors: Ioannis Houpis, Plainfield; Audrey Molina, Clark; Ralph P. Volante, Cranberry, all of N.J.

[73] Assignee: Merck & Co., Inc., Rahway, N.J.

[21] Appl. No.: 832,484

[22] Filed: Apr. 2, 1997

Related U.S. Application Data

[60] Provisional application No. 60/015,687, Apr. 17, 1996.
[51] Int. Cl.⁶ .............. C07D 213/38; C07D 213/30; C07D 213/26; C07D 213/24
[52] U.S. Cl. .............. 546/339; 546/330; 546/335; 546/337; 546/338; 546/340; 546/341; 546/342
[58] Field of Search .................. 546/330, 335, 546/337, 338, 339, 340, 341, 342

[56] References Cited

U.S. PATENT DOCUMENTS 5,622,977  4/1997  Werrellow et al. .......... 514/336

*Primary Examiner*—Patricia L. Morris
*Attorney, Agent, or Firm*—Curtis C. Panzer; David L. Rose

[57] ABSTRACT

A process for the preparation of a compound of structural formula I

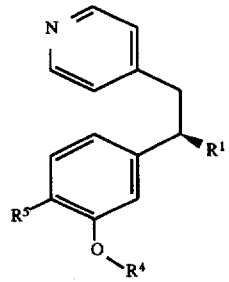

wherein $R^1$ is alkyl, alkenyl, phenyl or substituted phenyl, which comprises the addition of $R^1$ to an intermediate 2:

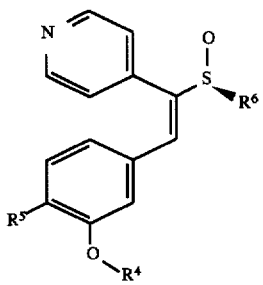

by treatment of 2 with $(R^1)_3M$ followed by reductive removal of the sulfinyl group.

3 Claims, No Drawings

METHOD OF PREPARING PHOSPHODIESTERASE IV INHIBITORS

This application claims the benefit of priority of U.S. Provisional application No. 60/015,687, filed Apr. 17, 1996.

BACKGROUND OF THE INVENTION

This application is directed to an improved process for making phosphodiesterase IV inhibitors such as those described in WO 94/14742, published Jul. 7, 1994.

Many hormones and neurotransmitters modulate tissue function by elevating intra-cellular levels of adenosine 3',5'- cyclic monophosphate (cAMP). The role of cyclic AMP (cAMP) as a second messenger is well recognized. It is responsible for transducing the effects of a variety of extra-cellular signals, including hormones and neurotransmitters. The level of intracellular cAMP is regulated through both its synthesis by adenyl cyclases and degradation by cyclic nucleotide phosphodiesterases (PDE). PDEs form a family of at least seven enzyme isotypes (I–VII) which differ in their affinity for cAMP and/or cGMP, subcellular localisation and regulation (Beavo J. A. and Reifsnyder D. H. (1990) *Trends Pharmacol. Sci.* 11 150–155; Conti M. et al., (1991) *Endocrine Rev.* 12 218–234). The clinical effects of a number of drugs can be rationalised on the basis of their selectivity for a particular PDE isotype. For example, the cardiotonic drugs milrinone and zaprinast are PDE III and PDE V inhibitors respectively. (Harrison S. A. et al., (1986) *Mol. Pharmacol.* 29 506–514; Gillespie P. G. and Beavo J. (1989) *Mol. Pharmacol.* 36 773–781). The anti-depressant drug, rolipram functions as a selective PDE IV inhibitor. (Schneider H. H. et al., (1986) *Eur. J. Pharmacol.* 127 105–115.).

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P. T. et al., (1992) *J. Immunol.* 148 2503–2510) and eosinophils (Dent G. et al., (1991) *Br. J. Pharmacol.* 103 1339–1346) and that inhibition of this isotype is associated with the inhibition of cell activation. Consequently PDE IV inhibitors are currently being developed as potential anti-inflammatory drugs particularly for the prophylaxis and treatment of asthma.

A prior art process for preparing compound I is as shown in the following reaction scheme:

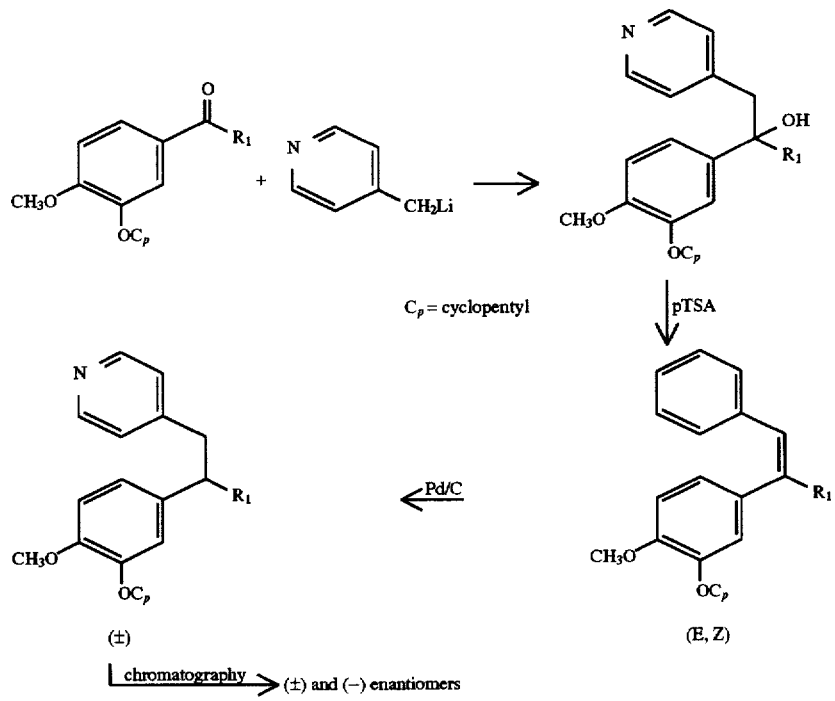

This process, involving resolution into the enantiomers as a last step necessarily means a commercially unacceptable yield of product.

Another prior art process employs a synthetic strategy using 2S-bornane-O10,2-sultan as a chiral auxiliary as shown below:

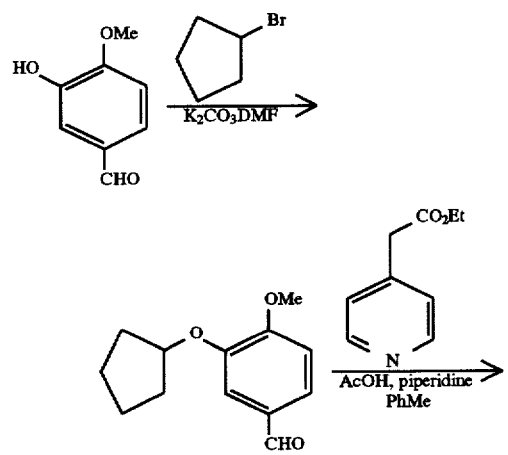

3
-continued

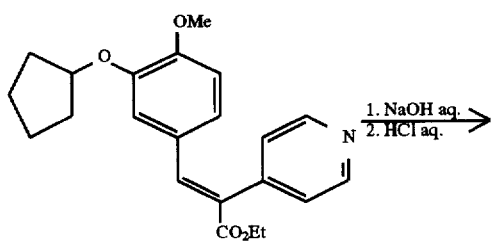

1. NaOH aq.
2. HCl aq.

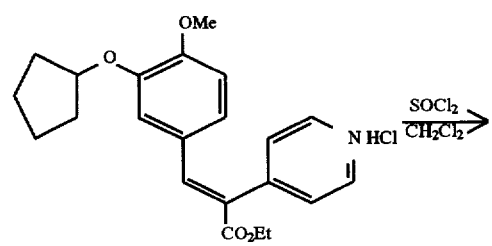

SOCl₂
CH₂Cl₂

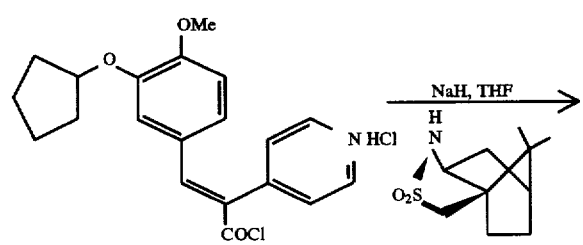

NaH, THF

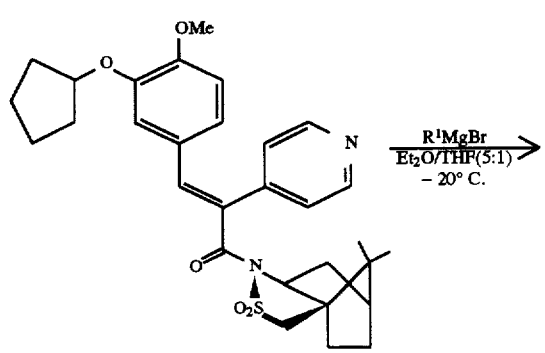

R¹MgBr
Et₂O/THF(5:1)
−20° C.

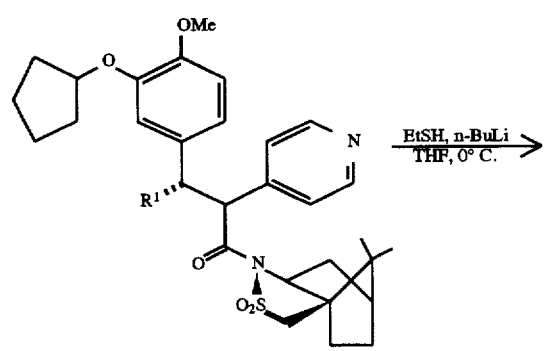

EtSH, n-BuLi
THF, 0° C.

4
-continued

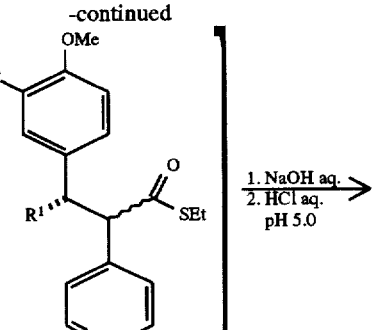

1. NaOH aq.
2. HCl aq.
pH 5.0

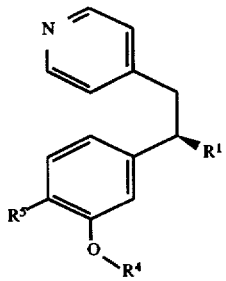

This method is not amenable to scale-up because of: the high price of the sultam; b) facile isomerization of the acid chloride during its preparation and/or the coupling reaction with the sultam, and c) extreme odor problem during the sultam cleavage using ethanethiol.

Now, with the present invention there is provided a chiral synthesis that produces Compound 1 in high yield and high enantiomeric excess.

SUMMARY OF THE INVENTION

This invention is concerned with a novel process for the preparation of a compound of structural formula I wherein $R^1$ is phenyl, substituted phenyl, $C_{1-6}$ alkyl or $C_{2-6}$ alkenyl which is an important antiasthmatic agent which comprises the key step of the addition of $R^1$ to an intermediate 2:

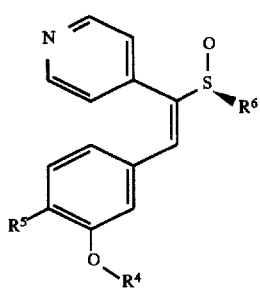

by treatment of 2 with $(R^1)_3M$ followed by reductive removal of the sulfinyl group.

DETAILED DESCRIPTION OF THE INVENTION

The novel process of this invention is depicted as follows:

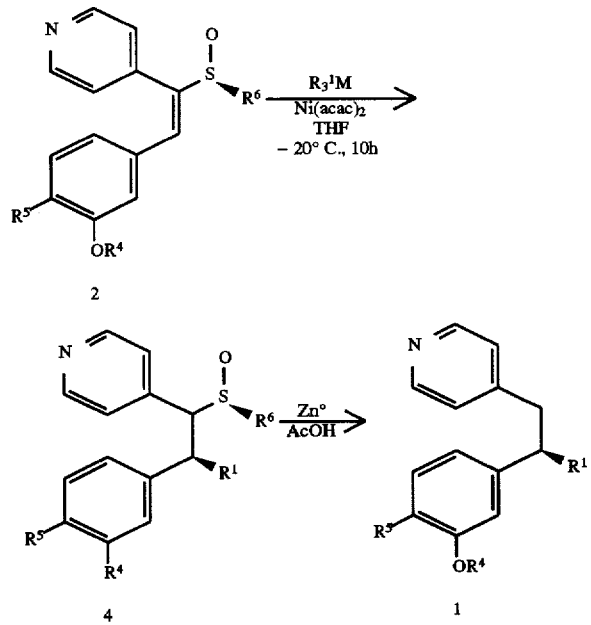

wherein:

$R^1$ is $C_{1-6}$ alkyl, $C_{2-6}$ alkenyl, phenyl, either unsubstituted or substituted with one or two substituents, which can be the same or different, selected from the group consisting of $R^2$ and $Alk(R^2)_m$;

wherein
$R^2$ is
1) halo,
2) —$N(R^3)_2$,
3) —$NO_2$,
4) —CN,
5) —$OR^3$,
6) —$C_{3-6}$ cycloalkoxy,
7) —$CO(R^3)$,
8) —$COOR^3$,
9) —$SR^3$,
10) —$SO_3H$,
11) —$SO_2(R^3)$,
12) —$SO_2N(R^3)_2$,
13) —$CON(R^3)_2$,
14) —$NHSO_2R^3$,
15) —$N(SO_2R^3)_2$,
16) —$NHSO_2N(R^3)_2$,
17) —$NHCOR^3$ or
18) —$NHCOOR^3$;

wherein

Alk is straight or branched chain $C_{1-6}$ alkylene, $C_{2-6}$ alkenylene or $C_{2-6}$ alkynylene, optionally interrupted by one, two or three —O—, —S—, —S(O)p or —$N(R^3)$—;

$R^3$ is hydrogen or $C_{1-6}$ alkyl or $C_{2-6}$ alkenyl;

$R^4$ is
1) $C_{3-6}$ cycloalkyl,
2) $C_{1-6}$ alkyl, or
3) $C_{1-6}$ alkenyl;

$R^5$ is
1) halo,
2) $CF_3$,
3) $C_{1-3}$ alkyl, or
4) $C_{1-3}$ alkoxy $R^6$ is
1) tolyl,
2) phenyl,
3) t-butyl, or
4) mesityl;

M is ZnLi or ZnMgBr.

m is zero or an integer selected from 1, 2 and 3; and p is an integer selected from 1 and 2.

The process comprises treating the olefin 2, and a catalyst, nickel acetylacetonate, Ni(acac)2, in an ethereal solvent such as THF, diethyl ether, glyme, or diglyme, preferably THF cooling to about $-35°$ to $-15°$ C. and adding a slurry of the zincate, $R^1{}_3M$, in the same ethereal solvent also at $-35°$ to $-15°$ C. while maintaining the temperature below about $-15°$ C. After aging for 20 to 30 hours the mixture is quenched with ammonium chloride solution and ethyl acetate and the pH adjusted to about 10 with a base, such as ammonium hydroxide, sodium or potassium hydroxide, a sodium or potassium carbonate. The product 4 is isolated from the organic layer, dissolved in an ethereal solvent preferably THF and an organic acid such as acetic acid, pivalic acid, trifluoroacetic chloroacetic acid, or propionic acid and treated with Zn metal. After quenching with water, an immiscible organic solvent such as methylene chloride, chloroform toluene, or ethylacetate is added and the pH is adjusted to about 6. The product, 1, is isolated from the organic layer.

The starting material, 2, is obtained according to the following reaction scheme:

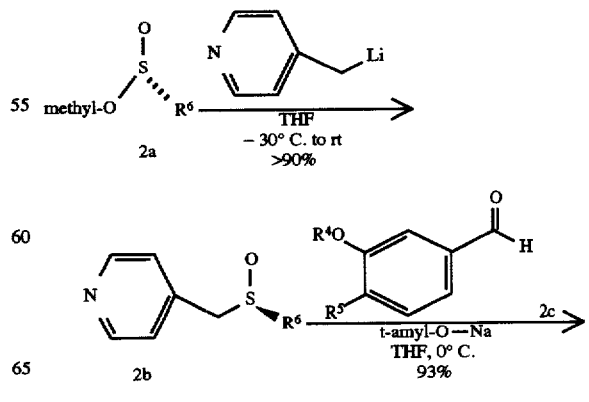

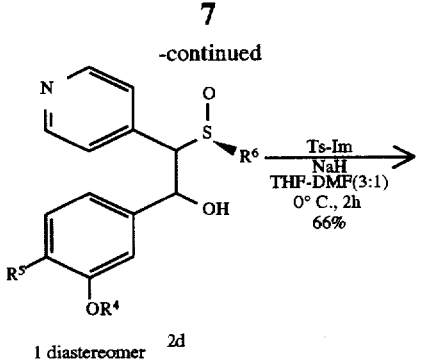

1 diastereomer 2d

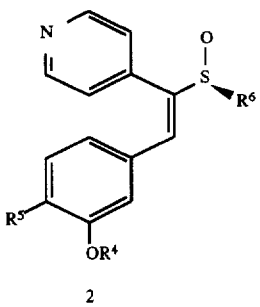

2

Complete details for preparation of 2 are provided in the Example that follows.

In this application "alkyl" means straight or branched alkyl with the indicated number of carbon atoms. "Halo" means chloro, bromo, fluoro or iodo.

EXAMPLE

Synthesis of tolylsulfinyl picoline 2b

| Materials | Amount | MW (d) | mmoles |
|---|---|---|---|
| 4-picoline | 30 mL | 93.13 (.957) | 306 |
| n-BuLi | 159 mL | 1.6M (Hexanes) | 255 |
| Menthyltoluene Sulfinate 2a | 30 g | 294.46 | 102 |

A solution of picoline in THF (351 mL) was cooled to −50° C. and treated with n-BuLi while maintaining the intenral temperature −45° C. The deep orange reacion mixture was warmed to ambient temperature and aged for 1 hr. The resulting dark solution was treated at 22° C. with a solution of the sulfinate in THF (120 mL) while maintaining the temperature <27° C. The reaction was aged for 30 min upon which time HPLC analysis indicated disappearance of the sulfinate 2a. The reaction mixture was quenced with 1M aqueous NH$_4$Cl (700 mL), CH$_2$Cl$_2$ (1000 mL) was added and the layers were partitioned. The organic layer was dried over Na$_2$SO$_4$ and concentrated in vacuo. The residue was flushed twice with hexane (2×200 mL) and then swished with hexanes (220 mL, 9 mL/g based on theoretical yield) to produce a thick white slurry which was aged overnight. The mixture was filtered, the cake was washed with hexanes (50 mL) and dried in vacuo at 38° C. to afford 21.46 g of the product (91%).

Synthesis of Aldol Adduct 2d

| Materials | Amount | MW | mmoles |
|---|---|---|---|
| Cyclopentylisovaniline 2c | 22.44 g | 220 | 102 |
| tolylsulfinyl picoline 2b | 21.46 | 231 | 93 |
| t-amyl ONa | 12.3 g | 110 | 112 |

A heterogeneous mixture of the aldehyde and sulfoxide in THF (235 mL) was cooled to −15° C. and treated with solid t-amylONa which resulted in a temperature increase to −8° C. HPLC analysis [sample must be quenched into a mixture of CH$_3$CN/1N-NH$_4$Cl(aq) to avoid the retro-aldol reaction which occurs in aqueous base] indicated that the reaction was complete in 15 minutes. The mixture was quenched with NH$_4$Cl(aq) (1M; 600 mL), CH$_2$Cl$_2$ (800 mL) was added, the layers were partitioned and the organic layer was dried over Na$_2$SO$_4$, filtered and concentrated in vacuo. The residue was flushed with heptane (150 mL) and then swished with 340 mL of 2:1 heptane-isopropyl acetate (8 mL/g based on theoretical yield) for 3 hours. The mixture was filtered and the cake was washed with heptane (100 mL) and dried in vacuo at 36° C. to afford 38.8 g of product (93%) as a single diastereomer.

Synthesis of Olefin 2

| Materials | Amount | MW | mmoles |
|---|---|---|---|
| Sulfoxide-alcohol 2d | 38.8 g | 451 | 86 |
| Tosylimidazole | 22.9 g | 222.3 | 103 |
| NaH | 5 g | 24 (80% in mineral oil) | 215 |
| Imidazole | 293 mg | 68 | 4.3 |

A solution of the sulfoxide-alcohol 2d in THF-DMF (3:2, 430 mL) was cooled to 0° C. and then treated successively with tosylimidazole, NaH and imidazole. Venting of the reaction vessel was essential to allow for hydrogen evolution. The mixture was aged for 2 hours at which time HPLC analysis shows that <2% of starting material remained. The reaction mixture was quenched with H$_2$O (60 mL) partitioned between ethyl acetate (500 mL) and H$_2$O (400 mL) and the organic layer dried over Na$_2$SO4, filtered and concentrated in vacuo. The residue was suspended in 365 mL of 2:1 heptane - isopropyl acetate and the slurry aged overnight. Filtration, washing with 2:1 heptane - isopropyl acetate (100 mL) was drying afforded 24.75 g of 2 (66%).

Synthesis of Adduct 4

| Materials | Amount | MW | mmoles |
|---|---|---|---|
| 2 | 0.5 g | 434 | 1.15 |
| ZnCl$_2$ | 4.6 mL | 0.5M (THF) | 2.3 |
| PhMgBr | 2.3 mL | 3M (Et$_2$O) | 6.9 |
| Ni(acac)$_2$ | 20.6 mg | 256.91 | 0.08 |

Ph$_3$ZnMgBr

A solution of ZnCl$_2$ in THF (0.5M solution) at 0° C. was treated with PhMgBr so that the temperture remained below 10° C. The resulting slurry was aged at 0° C. for 15 min and at ambient temperature for 10 min. The mixture was then cooled to −25° C.

Addition

A solution of the olefin-2 and Ni(acac)$_2$ in THF (3.5 mL) was cooled to −25° C. and treated with the Ph$_3$ZnMgBr slurry from above so that the internal temperature remained −22° C. The mixture was aged at <−27° C. for 25 hr upon which time HPLC analysis showed that <4A % of 2 remained. The mixture was quenched with NH₄Cl (30 mL), ethyl acetate (50 mL) was added and the pH was adjusted to about 10 with NH₄OH. The organic layer was separated and dried over Na₂SO₄, filtered and concentrated in vacuo. The residue was dissolved in 2.8 mL THF and 0.4 mL acetic acid and treated with Zn metal (160 mg) at ambient temperature. The reaction was aged for 1 hr at 25° C. at which time HPLC analysis indicated complete consumption of starting material. The reaction mixture was quenched with H₂O, CH₂Cl₂ was added and the pH adjusted to about 6 to produce two clear layers. [HPLC analysis indicated minimal losses of product in the aqueous layer.] The organic layer was dried over Na₂SO₄, filtered and concentrated in vacuo. Chromatography (1:1 hexane - ethyl acetate) afforded 1 (62%). Chiral HPLC analysis indicated a 92% enantiomeric excess (ee).

What is claimed is:

1. A process for the preparation of a compound of structural formula I:

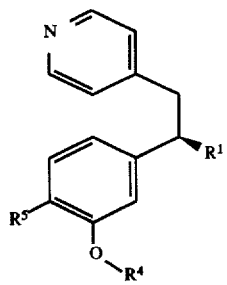

1 which comprises the steps of:

1) treating a compound of structural formula 2:

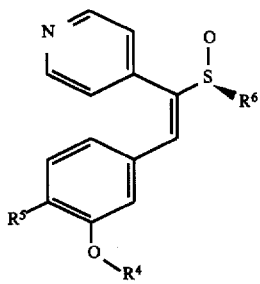

2 with a catalyst, Ni(acac)₂, in a ethereal solvent at −35° to −15° C. followed by treatment with a zincate of formula R¹₃M and aging for 20–30 hours to produce the adduct 4

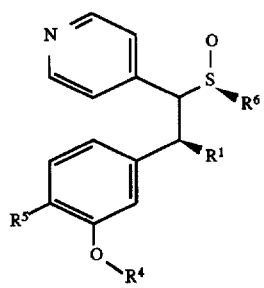

4

2) treating the adduct 4 in an ethereal solvent and an organic acid with Zn metal to produce the product, 1, wherein:

R¹ is $C_{1-6}$ alkyl, $C_{2-6}$ alkenyl, phenyl, either unsubstituted or substituted with one or two substituents, which can be the same or different, selected from the group consisting of R² and Alkl(R²)m wherein R² is
 1) halo,
 2) —N(R³)₂,
 3) —NO₂,
 4) —CN,
 5) —OR³,
 6) —$C_{3-6}$ cycloalkoxy,
 7) —CO(R³),
 8) —COOR³,
 9) —SR³,
 10) —SO₃H,
 11) —SO₂(R³),
 12) —SO₂N(R³)₂,
 13) —CON(R³)₂,
 14) —NHSO₂R³,
 15) —N(SO₂R3)₂,
 16) —NHSO₂N(R³)₂,
 17) —NHCOR³ or
 18) —NHCOOR³; wherein Alk is straight or branched chain $C_{1-6}$ alkylene, $C_{2-6}$ alkenylene or $C_{2-6}$ alkynylene, optionally interrupted by one, two or three —O—, —S—, —S(O)p or —N—(R³)—;

R³ is hydrogen or $C_{1-6}$ alkyl or $C_{2-6}$ alkenyl;

R⁴ is
 1) $C_{3-6}$ cycloalkyl,
 2) $C_{1-6}$ alkyl, or
 3) $C_{1-6}$ alkenyl;

R⁵ is
 1) halo,
 2) CF₃
 3) $C_{1-3}$ alkyl, or
 4) $C_{1-3}$ alkoxy

R⁶ is
 1) tolyl,
 2) phenyl,
 3) t-butyl, or
 4) mesityl;

M is ZnLi or ZnMgBr;

m is zero or an integer selected from 1, 2 and 3; and p is an integer selected from 1 and 2.

2. The process of claim 1 wherein M is ZnMgBr.

3. The process of claim 2, wherein R¹ is phenyl.

* * * * *